United States Patent
Postajian

(10) Patent No.: US 7,867,289 B2
(45) Date of Patent: Jan. 11, 2011

(54) COLD WAX DEPILATORY COMPOSITION AND RELATED PROCESS

(76) Inventor: Madlen Postajian, 2771 Community Ave., La Crescenta, CA (US) 91214

( * ) Notice: Subject to any disclaimer, the term of this patent is extended or adjusted under 35 U.S.C. 154(b) by 1905 days.

(21) Appl. No.: 11/059,075

(22) Filed: Feb. 15, 2005

(65) Prior Publication Data

US 2006/0182700 A1 Aug. 17, 2006

(51) Int. Cl.
*C14C 1/06* (2006.01)
(52) U.S. Cl. .......................... 8/161; 8/94.16; 424/70.1; 424/73
(58) Field of Classification Search .................. None
See application file for complete search history.

(56) References Cited

U.S. PATENT DOCUMENTS

| | | | |
|---|---|---|---|
| 3,949,067 A | 4/1976 | Gibbs | |
| 4,855,131 A | 8/1989 | Iris | |
| 5,154,919 A | 10/1992 | Des Garets | |
| 5,158,765 A | 10/1992 | Qasem | |
| 5,698,187 A * | 12/1997 | Naggiar | 424/73 |
| 6,074,647 A | 6/2000 | Zimmerman et al. | |
| 6,517,822 B1 | 2/2003 | Buck | |
| 2001/0001660 A1 | 5/2001 | Romero et al. | |
| 2004/0175340 A1 | 9/2004 | Gupta | |
| 2004/0180014 A1 | 9/2004 | Gupta | |

FOREIGN PATENT DOCUMENTS

EP 0649646 * 4/1995

* cited by examiner

*Primary Examiner*—Sharmila Gollamudi Landau
*Assistant Examiner*—Barbara Frazier
(74) *Attorney, Agent, or Firm*—Kelly Lowry & Kelley, LLP

(57) ABSTRACT

A method of preparing a depilatory composition includes placing a quantity of sucrose into a heating vessel. Vinegar and citric acid are added into the heating vessel in the respective amounts of about 30 to 35% and 2.0 to 2.5% of the quantity of sucrose. The sucrose, vinegar and citric acid are stirred to create a mixture. The mixture is heated to about 230 degrees Fahrenheit. The mixture is diluted with water in an amount of 2.0 to 2.5% of the quantity of sucrose. The diluted mixture is cooled to form a soft was a room temperature once the temperature of the diluted mixture reaches about 230 degrees Fahrenheit.

19 Claims, No Drawings

COLD WAX DEPILATORY COMPOSITION AND RELATED PROCESS

BACKGROUND OF THE INVENTION

The present invention relates to depilatories. More particularly, the present invention a depilatory composition of a wax-like consistency for use in removing hair from the human body.

Hair removal from certain locations on the human body seems to receive as much attention as the encouragement of hair growth on other parts of the human body. A long-running joke among middle-aged men is that as soon as they start losing hair on the top of their head, hair starts growing from other parts of their bodies where hair is not desired, such as their ears and nostrils. Both men and women face the problem of dealing with hair growing from areas of their bodies where hair growth is not desired. Hair and hair follicles can be removed by various processes such as electrolysis which provides a long-lasting solution. For centuries, women have removed unwanted facial hair and/or trimmed their eyebrows by plucking the hair from their body using tweezers. However, plucking and trimming is painful, provides only temporary benefits, and is not practical for removing large amounts of undesired hair growing on a person's back, arms, legs or the like.

In the past, various cold waxes, creams or the like have been used for hair removal. These formulations can be applied over greater areas of the human body for the purpose of hair removal than can be efficiently and timely addressed by plucking and these formulations also provide longer lasting effects. For example, U.S. Pat. No. 2,091,313 discloses a combination of honey, rosin and wax heated together and then mixed with citric acid until the mixture acquires a creamy texture. However, it is not disclosed what temperature the formulation is heated to. Also, a wax composition (e.g., beeswax) has been found to be a skin irritant that can cause inflamation. In another example, U.S. Pat. No. 4,832,949 discloses depilatory compositions formed from a mixture of honey, sugar and citric acid. However, these compositions must be heated so that they are softened prior to use.

Accordingly, there is a need for a depilatory composition that can be readily applied with a finger or fingers. There is a further need for a depilatory composition that can be readily removed by grasping and pulling quickly away from the skin to remove hair from the applied area. There is an additional need for a depilatory composition that is economical and easy to manufacture. The present invention fulfills these needs and provides other related advantages.

SUMMARY OF THE INVENTION

The present invention provides a depilatory composition that can be readily applied with a finger or fingers and readily removed by grasping and pulling quickly away from the skin to remove hair from the applied area. A depilatory composition embodying the present invention is economical and easy to manufacture.

A method of preparing a depilatory composition includes placing a quantity of sucrose into a heating vessel. Vinegar and citric acid are added into the heating vessel in the respective amounts of about 30 to 35% and 2.0 to 2.5% of the quantity of sucrose. The sucrose, vinegar and citric acid are stirred to create a mixture. The mixture is heated to about 230 degrees Fahrenheit. The mixture is diluted with water in an amount of 2.0 to 2.5% of the quantity of sucrose. The diluted mixture is cooled to form a soft wax at room temperature once the temperature of the diluted mixture reaches about 230 degrees Fahrenheit.

During heating, the temperature of the mixture is monitored by positioning a thermometer in the mixture, and checking thermometer readings as the mixture cooks.

Diluting the mixture with water requires that the water be added to the mixture when the mixture reaches about 210 degrees Fahrenheit. The water is also stirred into the mixture. The water is added to the mixture about 10-15 minutes after heating the mixture commences, and heating the diluted mixture for about 5 minutes or less.

In one embodiment of the present invention, the heating vessel comprises an electric pot set to a temperature of about 270 degrees Fahrenheit.

The quantities of the ingredients are proportional with respect to the amount of sucrose being used. For example, where the quantity of sucrose is about 96 fluid ounces of sucrose, the amount of water is within the range of 2.0 to 2.5 fluid ounces of room temperature water, the amount of vinegar is about 32 fluid ounces of vinegar; and the amount of citric acid is within the range of 2.0 to 2.5 fluid ounces of citric acid. The vinegar may come in various forms including, without limitation, apple cider vinegar. Likewise, the citric acid may come in various forms including, without limitation, lemon juice.

Prior to skin application, the soft wax is warmed. The soft wax is manually applied in thin strips to the skin. Each applied strip is removed immediately after application to the skin.

Other features and advantages of the present invention will become apparent from the following more detailed description.

DETAILED DESCRIPTION OF THE PREFERRED EMBODIMENT

A method of preparing a depilatory composition is described that provides reduces the effort required to carry the articles. This composition is usable on any part of the human body/skin where undesirable hair is located.

The present invention resides in a method of preparing a depilatory composition that includes placing a quantity of sugar into a heating vessel. The sugar comes in various types including, but not limited to, sucrose, fructose, glucose, dextrose and the like. The sugar may also come in various forms such as white granulated (fine or course) sugar, brown granulated (fine or course) sugar, powdered sugar, baker's sugar, unprocessed sugar and the like. The sugar may be derived from various sources including, but not limited to, sugar cane, sugar beet, sugar Maple, corn and the like. Corn syrup and molasses are other alternatives. Sugar that is in 'dry' form (e.g., granulated crystals, powder) may be made into a liquid or paste by adding an appropriate amount of water to the 'dry' sugar. Likewise, 'syrupy' sugar (e.g., corn syrup, molasses) may also be made into a less viscous liquid form by adding an appropriate amount of water. Various heating vessels may be used including, but not limited to an electric pot, a kettle, vat or other container that can be placed on a heating device such as an electric or gas stove, electric hot plate or the like. Preferably, the heating vessel comprises an electric pot that is capable of being set to heat the contents of the pot to a temperature of at least as high as about 270 degrees Fahrenheit, if not higher. Both commercial and non-commercial heating vessels may be used, depending on whether the user desires to manufacture large commercial-sized quantities or smaller personal-sized quantities of the composition.

In the preparation of the composition embodying the present invention, a quantity of sucrose is combined with a limited quantity of citric acid and vinegar in the heating vessel. Other ingredients, including vinegar and citric acid, are added into the heating vessel. The vinegar and citric acid are added in the respective amounts of about 30 to 35% and 2.0 to 2.5% of the quantity of sucrose. Later on, a quantity of water is added to dilute these ingredients.

The quantities of the vinegar and citric acid are proportional with respect to the amount of sucrose being used. For example, where the quantity of sucrose is about 96 fluid ounces (about 12 cups) of sucrose, the amount of vinegar is about 32 fluid ounces (about 4 cups) of vinegar; and the amount of citric acid is within the range of 2.0 to 2.5 fluid ounces of citric acid. The vinegar may come in various forms including, without limitation, apple cider vinegar, grape vinegar or the like. Likewise, the citric acid may come in various forms including, without limitation, lemon juice, orange juice, lime juice or the like.

The sucrose, vinegar and citric acid are briefly stirred to create a mixture. Once the ingredients are mixed, the heating vessel is turned on and set so as to heat the mixture to about 270 degrees Fahrenheit. At this point the mixture has a watery consistency. The color of the mixture at this time is light honey color if the vinegar used is apple cider vinegar which has a color similar to apple juice. The color of the mixture may vary according to the type of sugar, vinegar and/or citric acid used. As the mixture is cooking, the mixture may be stirred occasionally.

The mixture is heated to about 230 degrees Fahrenheit. During heating, the temperature of the mixture is monitored by positioning a thermometer in the mixture, and checking thermometer readings as the mixture cooks. The mixture is diluted with water in an amount of 2.0 to 2.5% of the quantity of sucrose when the mixture of sucrose, citric acid and vinegar reaches about the range of 210 to 230 degrees Fahrenheit. The water is added to the mixture about 10-15 minutes after heating the mixture commences. In the above example where about 96 fluid ounces of sucrose is used, the amount of water is within the range of 2.0 to 2.5 fluid ounces of room temperature water. The water may be tap water, spring water, distilled water or the like. Diluting the mixture with water requires that the water be added to the mixture when the mixture reaches about 210 degrees Fahrenheit. The water is also stirred into the mixture, which reduces the temperature of the mixture, and so the diluted mixture is heated for about an additional 5 minutes or less. The mixture is stirred as the diluted mixture is cooking. This allows the diluted mixture to be homogenous as the mixture heats up again. The diluted mixture is cooled to form a soft wax at room temperature once the temperature of the diluted mixture reaches the range of about 230 to 250 degrees Fahrenheit.

At this point, the heat is turned off and the contents of the heating vessel (i.e., the diluted mixture) is immediately and readily poured from the heating vessel into a number of appropriate individual containers. The resultant mixture has a generally homogenous appearance during cooking in terms of color from start to finish. The mixture during the cooking process becomes a slightly darker honey color. The consistency of the diluted mixture at the time the mixture is poured into the containers is similar to that of maple syrup. Once the diluted mixture has cooled in the containers to room temperature, the consistency thickens and becomes like a soft wax and the containers may then be sealed by a lid or the like. The color of the soft wax after cooling is also a warm honey color. The resultant soft wax from the cooled mixture is pliable and easy to work. The soft wax stored in the individual closed containers can be stored for an indefinite period of time before use. In the above example, a mixture that uses about 96 fluid ounces of sugar can result in about 96 fluid ounces of soft wax which can fill approximately six containers containing 16 fluid ounces each of the soft wax. The number of containers filled depends on the size of the containers used. Once the lids are on the containers, the containers may be labeled and shipped.

The soft wax may be removed from the container by the user scooping the soft wax out using their fingers. In order to increase ease of use, prior to skin application, the soft wax is warmed. The soft wax may be directly applied to the area of skin with the undesired hair or the soft wax may first be shaped by pulling, stretching or kneading the soft wax to match the area of skin the wax is to be applied to. Either way, the soft wax is manually applied, preferably in relatively thin, elongated strips about the size of a BAND-AID, to the skin. The soft wax is pressed to the skin with sufficient pressure so as to assure uniform adherence of the unwanted hair to the wax along the strip from which the hair is to be removed. Each applied strip is removed immediately after application to the skin by quickly pulling the strip off by hand. The application procedure described above is then repeated, as necessary and/or desired, over or along adjacent areas of the skin where the user desires to remove unwanted hair. Once the unwanted hair has been removed, the user may close their skin's pores and/or soothe their skin using any number of conventional means such as applying a wet cold cloth or the like to the treated area.

The above-described embodiments of the present invention are illustrative only and not limiting. It will thus be apparent to those skilled in the art that various changes and modifications may be made without departing from this invention in its broader aspects. Therefore, the appended claims encompass all such changes and modifications as falling within the true spirit and scope of this invention.

What is claimed is:

1. A method of preparing a depilatory composition, comprising the steps of:
   placing a quantity of sucrose into a heating vessel;
   adding vinegar in an amount of about 30 to 35%, and citric acid in an amount of 2.0 to 2.5% of the quantity of sucrose, into the heating vessel;
   stirring the sucrose, vinegar and citric acid to create a mixture;
   heating the mixture to about 230 degrees Fahrenheit;
   diluting the mixture with water in an amount of 2.0 to 2.5% of the quantity of sucrose; and
   cooling the diluted mixture to form a soft wax at room temperature once the temperature of the diluted mixture reaches about 230 degrees Fahrenheit.

2. The method of claim 1, wherein the heating step includes the step of monitoring temperature of the mixture by positioning a thermometer in the mixture, and checking thermometer readings as the mixture cooks.

3. The method of claim 1, wherein the diluting step includes the steps of adding the water to the mixture when the mixture reaches about 210 degrees Fahrenheit, and stirring the water into the mixture.

4. The method of claim 1, wherein the diluting step includes the steps of adding the water to the mixture about 10-15 minutes after heating the mixture commences, and heating the diluted mixture for about 5 minutes or less.

5. The method of claim 1, wherein the heating vessel comprises an electric pot set to a temperature of about 270 degrees Fahrenheit.

6. The method of claim 1, wherein the amount of water is within the range of 2.0 to 2.5 fluid ounces of room temperature water, the quantity of sucrose is about 96 fluid ounces of sucrose, the amount of vinegar is about 32 fluid ounces of vinegar; and the amount of citric acid is within the range of 2.0 to 2.5 fluid ounces of citric acid.

7. The method of claim 1, wherein the vinegar comprises apple cider vinegar, and the citric acid comprises lemon juice.

8. The method of claim 1, including the steps of warming the soft wax prior to skin application, manually applying the soft wax in thin strips to the skin, and removing each applied strip immediately after application to the skin.

9. A method of preparing a depilatory composition, comprising the steps of:
   placing a quantity of sucrose into a heating vessel;
   adding vinegar in an amount of about 30 to 35%, and citric acid in an amount of 2.0 to 2.5% of the quantity of sucrose, into the heating vessel;
   stirring the sucrose, vinegar and citric acid to create a mixture;
   heating the mixture to about 230 degrees Fahrenheit;
   diluting the mixture with water in an amount of 2.0 to 2.5% of the quantity of sucrose;
   adding the water to the mixture when the mixture reaches about 210 degrees Fahrenheit;
   stirring the water into the mixture;
   cooling the diluted mixture to form a soft wax at room temperature once the temperature of the diluted mixture reaches about 230 degrees Fahrenheit;
   warming the soft wax prior to skin application;
   manually applying the soft wax in thin strips to the skin; and
   removing each applied strip immediately after application to the skin.

10. The method of claim 9, wherein the heating step includes the step of monitoring temperature of the mixture by positioning a thermometer in the mixture, and checking thermometer readings as the mixture cooks.

11. The method of claim 9, wherein the diluting step includes the step of adding the water to the mixture about 10-15 minutes after heating the mixture commences, and warming the soft wax prior to skin application.

12. The method of claim 9, wherein the heating vessel comprises an electric pot set to a temperature of about 270 degrees Fahrenheit.

13. The method of claim 9, wherein the amount of water is within the range of 2.0 to 2.5 fluid ounces of room temperature water, the quantity of sucrose is about 96 fluid ounces of sucrose, the amount of vinegar is about 32 fluid ounces of vinegar; and the amount of citric acid is within the range of 2.0 to 2.5 fluid ounces of citric acid.

14. The method of claim 9, wherein the vinegar comprises apple cider vinegar, and the citric acid comprises lemon juice.

15. A method of preparing a depilatory composition, comprising the steps of:
   placing about 96 fluid ounces of sucrose into a heating vessel comprising an electric pot set to a temperature of about 270 degrees Fahrenheit;
   adding about 32 fluid ounces of vinegar, and a range of 2.0 to 2.5 fluid ounces of citric acid into the heating vessel;
   stirring the sucrose, vinegar and citric acid to create a mixture;
   heating the mixture to about 230 degrees Fahrenheit;
   diluting the mixture with a range of 2.0 to 2.5 fluid ounces of room temperature water; and
   cooling the diluted mixture to form a soft wax at room temperature once the temperature of the diluted mixture reaches about 230 degrees Fahrenheit.

16. The method of claim 15, wherein the vinegar comprises apple cider vinegar, and the citric acid comprises lemon juice.

17. The method of claim 15, including the steps of warming the soft wax prior to skin application, manually applying the soft wax in thin strips to the skin, and removing each applied strip immediately after application to the skin.

18. The method of claim 15, wherein the heating step includes the steps of monitoring temperature of the mixture by positioning a thermometer in the mixture, and checking thermometer readings as the mixture cooks; and the diluting step includes the steps of adding the water to the mixture when the mixture reaches about 210 degrees Fahrenheit, and stirring the water into the mixture.

19. The method of claim 18, wherein the diluting step includes the step of adding the water to the mixture about 10-15 minutes after heating the mixture commences, and warming the soft wax prior to skin application.

* * * * *